(12) United States Patent
Tamminga et al.

(10) Patent No.: US 9,110,072 B2
(45) Date of Patent: Aug. 18, 2015

(54) ASSEMBLY OF A CARTRIDGE AND A CARTRIDGE CLAMP, AND A CARTRIDGE CLAMP FOR USE IN SUCH AN ASSEMBLY

(75) Inventors: Peter S. Tamminga, Emmen (NL); Jeroen Camstra, Emmen (NL)

(73) Assignee: SPARK HOLLAND B.V., Emmen (NL)

(*) Notice: Subject to any disclaimer, the term of this patent is extended or adjusted under 35 U.S.C. 154(b) by 518 days.

(21) Appl. No.: 13/568,671

(22) Filed: Aug. 7, 2012

(65) Prior Publication Data

US 2013/0037476 A1 Feb. 14, 2013

Related U.S. Application Data

(60) Provisional application No. 61/522,697, filed on Aug. 12, 2011.

(30) Foreign Application Priority Data

Aug. 12, 2011 (EP) .................................. 11177373

(51) Int. Cl.
*G01N 30/60* (2006.01)
*B01J 20/281* (2006.01)
*G01N 30/00* (2006.01)

(52) U.S. Cl.
CPC ........ *G01N 30/6026* (2013.01); *G01N 30/6091* (2013.01); *B01J 20/281* (2013.01); *G01N 2030/009* (2013.01)

(58) Field of Classification Search
CPC .... B01D 27/00; B01D 29/00; G01N 30/6026; G01N 30/6091; G01N 2030/009; B01J 20/281

USPC .................................................. 210/435, 446
See application file for complete search history.

(56) References Cited

U.S. PATENT DOCUMENTS

| | | | |
|---|---|---|---|
| 5,651,885 A * | 7/1997 | Schick ........................ | 210/198.2 |
| 6,117,329 A | 9/2000 | Hargro | |
| 2011/0008224 A1* | 1/2011 | Gulers .......................... | 422/527 |
| 2011/0094953 A1* | 4/2011 | Doehren et al. .......... | 210/198.2 |

FOREIGN PATENT DOCUMENTS

| | | |
|---|---|---|
| EP | 2 278 325 A1 | 1/2011 |
| WO | WO 00/54023 A1 | 9/2000 |
| WO | WO 02/35132 A2 | 5/2002 |
| WO | WO 2005/087339 A1 | 9/2005 |

* cited by examiner

*Primary Examiner* — Fred Prince
(74) *Attorney, Agent, or Firm* — Oliff PLC

(57) ABSTRACT

An assembly of a cartridge and a cartridge clamp is disclosed. The cartridge has a cartridge body bounding a passage extending from a first end face to a second end face of the cartridge body. The cartridge clamp has a first and second clamping jaw comprising a first and second clamping face, respectively. A first and a second conduit are connected to the first and second clamping jaw, respectively. Said cartridge clamp is adapted for clamping said cartridge in-between the first and the second clamping face and for forming a closed circuit composed of the first conduit, the passage and the second conduit during clamping. Each clamping face has a ring-shaped protrusion extending around the end aperture of the respective conduit. The cartridge body is completely made of PEEK and each ring-shaped protrusion has a contact end face.

19 Claims, 4 Drawing Sheets

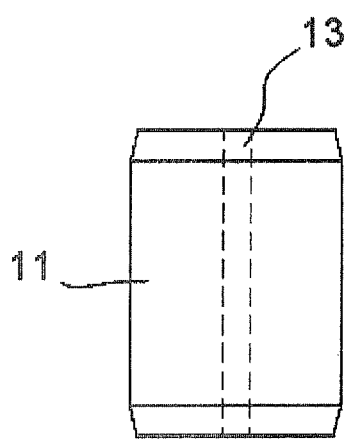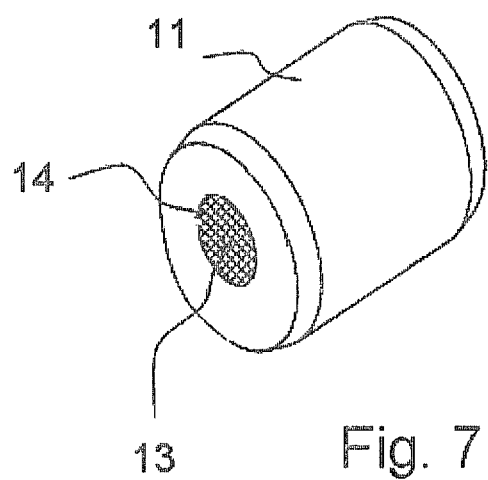
Fig. 6
Fig. 7

ASSEMBLY OF A CARTRIDGE AND A CARTRIDGE CLAMP, AND A CARTRIDGE CLAMP FOR USE IN SUCH AN ASSEMBLY

FIELD AND BACKGROUND OF THE INVENTION

The invention relates to an assembly of a cartridge and a cartridge clamp as described in the preamble of claim 1.

Such an assembly is known from EP-A-2,278,325. This assembly of which the cartridge is sometimes called a flow through cartridge is used for selecting an analyte online with high performance liquid chromatography (HPLC) based on solid phase extraction (SPE). The cartridge clamp of the known assembly comprises clamping jaws having sharp circular ribs which during clamping are driven into the end faces of the cartridge for fixing and sealing. The cartridge of the known assembly has a cartridge body comprising a core of a first material and sealing rings constituting surface portions of the end faces of the cartridge body, which sealing rings are made of a second material. During clamping, clamping pressures of about 2500 N may be applied on the sealing rings by the clamping jaws and pressures of up to 100 MPa may be applied to the passage through the cartridge body to perform SPE. At such high pressures the HPLC is called UHPLC (ultra high performance liquid chromatography) and amongst other things sample loading can be sped up and cycle time is reduced. To prevent leakages from occurring as a result of such high pressures EP-A-2,278,325 teaches that the first material is stronger and stiffer than the second material. Since the second material, e.g., aliphatic polyamide (NYLON), polytetrafluoroethylene (PTFE) or polyvinylidene difluoride (PVDF) is more flexible than the first material, e.g., polyether ether ketone (PEEK) or fiber reinforced polyphenylene sulfide (PPS), a hermetic seal between the clamping faces of the clamping jaws and the end faces of the cartridge is, according to EP-A-2,278,325, reliably obtained. Although the known assembly performs satisfactory at such high pressures it appears that in some cases leakage occurs between the sealing rings and cartridge body.

SUMMARY OF THE INVENTION

It is an object of the present invention to provide an assembly of a cartridge and a cartridge clamp with an improved resistance against leakage at high pressures.

According to the invention, this object is achieved by providing an assembly according to claim 1. Since the cartridge body is completely made of PEEK or of a single material having a density, a Young's-modulus, a tensile strength, a water absorption, a thermal degradation and a chemical resistance substantially similar to PEEK, and each ring-shaped protrusion has a contact end face for contacting a contact surface of the end face of the cartridge body, said contact end face comprising a flat surface part, said flat surface part being parallel to the end face of the cartridge body during clamping for creating a positive mechanical engagement between the clamping face and the respective contact surface of said respective end face of the cartridge body during clamping of the cartridge between the clamping jaws it appears that the PEEK material during clamping applies sufficient contra-pressure against the ring-shaped protrusion so that with a contact end face having a flat surface part a more reliable sealing is provided than as provided by the assembly known from EP-A-2,278,325. Using a sharp circular rib as protrusion as e.g. disclosed in EP-A-2,278,325 would result in an undesired plastic deformation of the PEEK material. Because of this plastic deformation the PEEK material cannot apply sufficient contra-pressure during clamping to ensure a reliable sealing. It thus appears that the shape of the ring-shaped protrusion has to be such that a positive mechanical engagement is obtained, so that the PEEK material at the contact surface is at least partly elastically deformed to obtain a reliable sealing. Since according to the invention the ring-shaped protrusion comprises a flat surface part parallel to the end face of the cartridge body during clamping a reliable sealing can be obtained. Excellent sealing results are obtained when the flat surface part has a radial dimension between about 0.15 and about 0.25 mm. When the radial dimension is about 0.2 mm it is even possible to use one cartridge twice for performing SPE at such high pressures.

In an advantageous embodiment of an assembly according to the invention each of the edges of the flat surface part is rounded. This facilitates loosening the cartridge from the clamping surface after SPE has been completed.

In particular when the assembly comprises means for circulating a liquid through the closed circuit with a liquid pressure of at least 100 MPa, and the cartridge clamp is adapted for clamping said cartridge in-between the first and the second clamping face with a clamping force of at least 1500 N, preferably at least 1900 N, more preferably at least 2300 N, and most preferably of about 2500 N, the reliable sealing can be maintained for about two clamp cycles of 20 minutes ensuring that a correct SPE is obtained. Depending on the liquid used the value of the clamping force necessary to obtain a reliable sealing can vary, but in most cases a clamping force of 2300 N ensures reliable sealing for all liquids.

In a preferred embodiment of an assembly according to the invention each ring-shaped protrusion has a height between about 0.16 and 0.23 mm resulting in a reliable sealing during clamping. When the height is about 0.2 mm it is even possible to use one cartridge twice for performing SPE at such high pressures.

In an advantageous embodiment of an assembly according to the invention each ring-shaped protrusion is slanted with an angle between about 6° and 12°, which facilitates removing the cartridge from the clamping jaws after SPE has been completed.

In a further preferred embodiment of an assembly according to the invention the cartridge has a diameter of about 8 mm, the passage of the cartridge has a diameter of about 1 mm, and the inner diameter of each ring-shaped protrusion is about 4 mm. Using this specific cartridge prevents that during clamping PEEK material is forced towards and into the passage, which would result in insufficient contra-pressure of the PEEK material against the ring-shaped protrusions which would adversely effect the sealing.

In a still further embodiment of an assembly according to the invention each ring-shaped protrusion has an inner height and an outer height, wherein the inner height is smaller than the outer height. As a result during clamping PEEK material is forced in a more radial outward direction, where the cartridge body contains more material, which provides sufficient counter-pressure to ensure a correct positive mechanical engagement. Most preferably the inner height is about 0.2 mm and the outer height is about 0.5 mm.

In an advantageous embodiment of an assembly according to the invention the cartridge comprises at least one sieve having a diameter of at most about 3 mm welded to an end face of the cartridge body, said sieve being substantially coaxial with the passage. As a result of the sieve being smaller than 3 mm in diameter it is prevented that as a result of the ultra high liquid pressure the sieve is loosened from the end face of the cartridge body.

Although PEEK is at the moment the most preferred material to be used in the assembly according to the invention, the invention is equally applicable to cartridge bodies in which the PEEK is replaced by a cartridge completely made of a single material having a density, a Young's-modulus, a tensile strength, a water absorption, a thermal degradation and a chemical resistance substantially similar to PEEK.

The present invention further relates to a cartridge clamp for use in an assembly according to the invention, wherein said cartridge clamp has a first clamping jaw comprising a first clamping face and a second clamping jaw comprising a second clamping face, said first and second clamping faces being opposite of each other and facing each other, at least one clamping jaw being mounted to a slide movable along guides towards and away from the other clamping jaw, respectively, a first conduit being connected to the first clamping jaw and a second conduit being connected to the second clamping jaw, said conduits extending through the respective clamping jaw and each having an end aperture in the clamping face of the respective clamping jaw, said cartridge clamp being adapted for clamping a cartridge having a cartridge body and a passage in-between the first and the second clamping face and for forming a closed circuit composed of the first conduit, the passage and the second conduit during clamping, each clamping face having a ring-shaped protrusion extending around the end aperture of the respective conduit, said protrusions being arranged for each contacting and deforming end faces of a cartridge body when a cartridge is clamped between the clamping jaws, characterized in that each ring-shaped protrusion has a contact end face comprising a flat surface part. In a preferred embodiment of the cartridge clamp according to the invention the flat surface part has a radial dimension between about 0.15 and about 0.25 mm, preferably said radial dimension is about 0.2 mm. It is advantageous when each of the edges of the flat surface part is rounded. It is furthermore advantageous when the cartridge clamp is adapted for clamping a cartridge in-between the first and the second clamping face with a clamping force of at least 1500 N, preferably at least 1900N, more preferably at least 2300, and most preferably of about 2500 N. Preferably each ring-shaped protrusion has a height between about 0.16 and 0.23 mm, preferably said height is about 0.2 mm. In a further advantageous embodiment of a cartridge clamp according to the invention each ring-shaped protrusion is slanted with an angle between about 6° and 12°. Preferably the cartridge has a diameter of about 8 mm, wherein the passage of the cartridge has a diameter of about 1 mm, and wherein the inner diameter of each ring-shaped protrusion is about 4 mm. In a further embodiment of a cartridge clamp according to the invention each ring-shaped protrusion has an inner height and an outer height, and wherein the inner height is smaller than the outer height. Preferably the inner height is about 0.2 mm and the outer height is about 0.5 mm.

Particular elaborations and embodiments of the invention are set forth in the dependent claims.

Further features, effects and details of the invention appear from the detailed description and the drawings.

BRIEF DESCRIPTION OF THE DRAWINGS

FIG. 6 is a diagrammatic side view of the cartridge shown in FIG. 2; and

FIG. 7 is a perspective view of a cartridge with a sieve.

DETAILED DESCRIPTION

Figure 1:
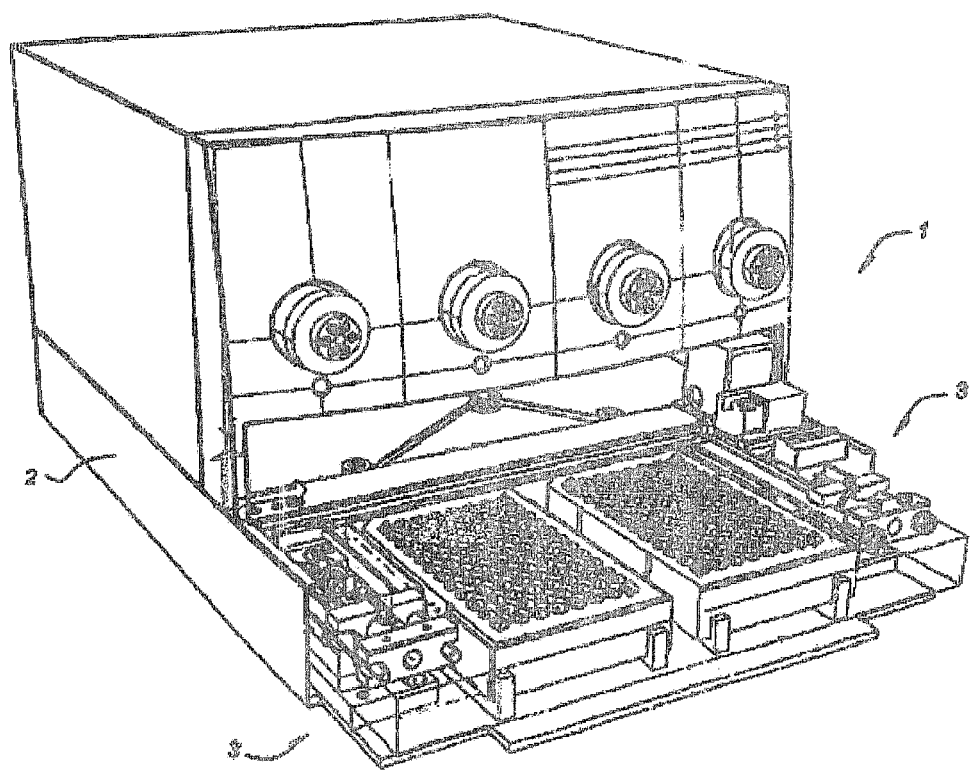
FIG. 1 is a perspective view representation of an example of an SPE instrument in which the assembly according to the invention is installed.
Figure 2:
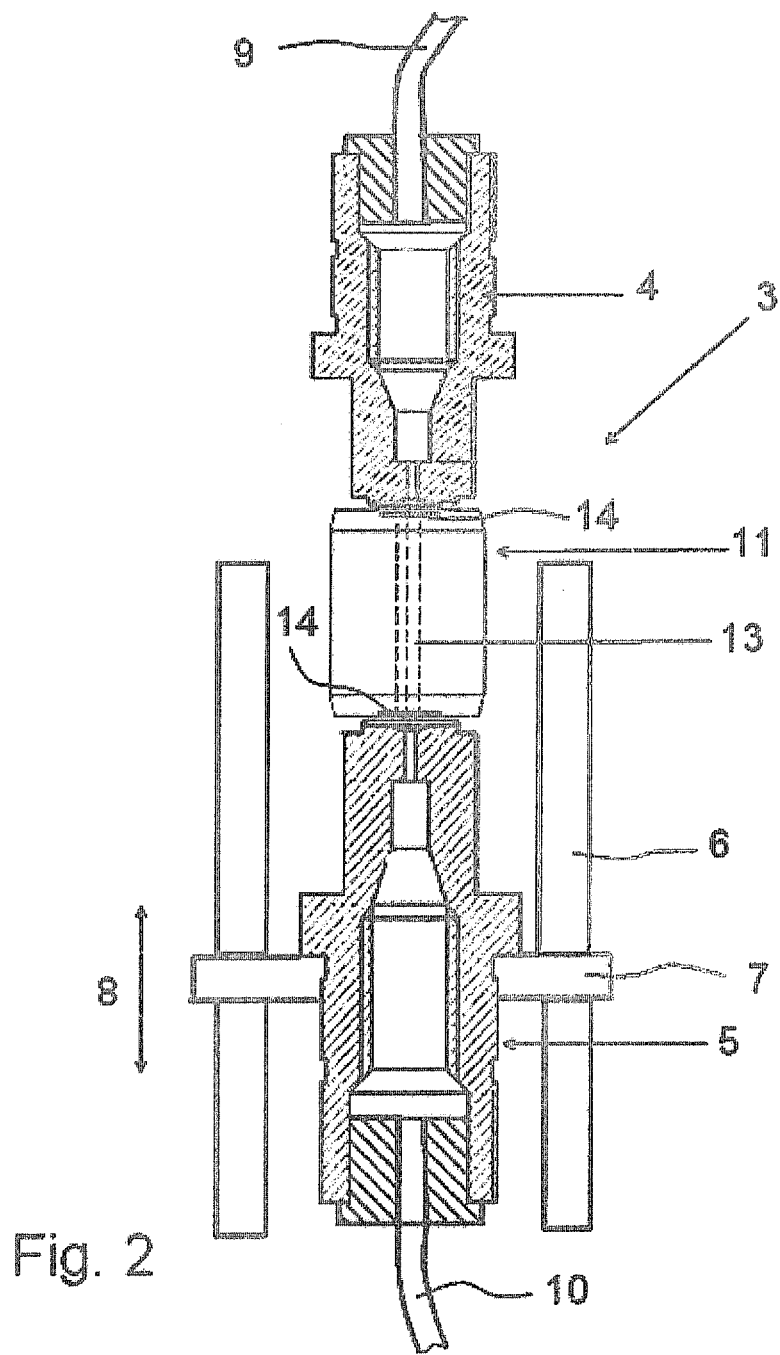
FIG. 2 is a diagrammatic top plan view of a cartridge clamp and a cartridge being part of the assembly according to the invention.

FIG. 1 shows an example of a solid phase extraction (SPE) instrument 1 with cartridges according to the present invention. The SPE instrument has a housing 2 and a cartridge holder 3 on the left and right-hand side of the open front of the housing 2. As is best seen in FIG. 2, each of these cartridge holders 3 has two clamping jaws 4 and 5, of which a first clamping jaw 4 is fixed relative to the housing (at least during operation) and a second clamping jaw 5 is mounted to a slide 7 movable along guides 6. The slide 7 is movable in a reciprocating way along the guides 6 with the clamping jaw 5 as indicated by a double arrow 8. A first conduit 9 is connected to first clamping jaw 4 and a second conduit 10 is connected to second clamping jaw 5. The conduits 8 and 9 extend through the clamping jaws 4 and 5 and have end apertures in frontal clamping faces of the clamping jaws 4 and 5, which frontal faces face each other.

When the clamping jaws 4 and 5 have been moved apart, a cartridge 11 having a cartridge body can be placed between the jaws 4, 5, after which clamping jaw 5 can be moved towards clamping jaw 4 in order to clamp the cartridge 11 between the clamping jaws 4 and 5. The cartridge body is completely made of PEEK, and consequently the cartridge body is identical to the cartridge. The cartridge 11 is an essentially cylindrical body through which a passage or channel 13 extends in axial direction of the cartridge 11 from the first end face to the second, opposite end face of the cartridge 11. In this example two sealing membranes or sieves 14 at opposite ends of the passage 13 retain a sorbent in-between. When the cartridge 11 is clamped between the jaws 4, 5, the conduits 9, 10 are in communication with the channel 9 forming a closed circuit so that a liquid can be supplied via the conduit 9, passed through the cartridge 11 and discharged via the conduit 10, or conversely, supplied via the conduit 10, passed through the cartridge 11 and discharged via the conduit 9.

When the cartridge 11 is clamped between the clamping jaws 4, 5, ring-shaped protrusions 12 (FIGS. 3-5) extending around the end aperture of the respective conduit of the clamping jaws 4, 5 are pressed into end faces of the cartridge 11, sealing end faces of the cartridge 11 against the jaws 4, 5.

Said ring-shaped protrusions 12 are arranged for each contacting and deforming the end faces of the cartridge 11 when the cartridge 11 is clamped between the clamping jaws 4, 5 with the passage 13 of the cartridge 11 aligned with the apertures in the clamping faces as shown in FIG. 2.

The jaws 4, 5 can be released from the cartridge 11 to allow the cartridge to be removed from between the jaws 4, 5.

During SPE, the cartridge 11 is exposed to essentially the full pressure at which an eluent is pressed through the closed circuit. The pressure applied in UHPLC is up to 100 MPa, sometimes even 120 MPa or more. UHPLC is becoming increasingly important for the analysis of complex samples because of its high separation power, and because sample loading can be sped up and cycle time can be reduced.

Figure 3:
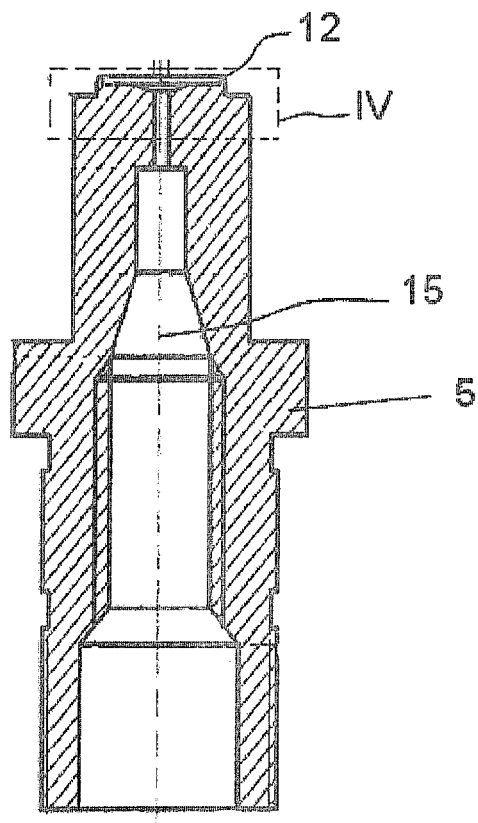
FIG. 3 is a side view in cross-section of a clamping jaw of the cartridge clamp shown in FIG. 2.
Figure 4:
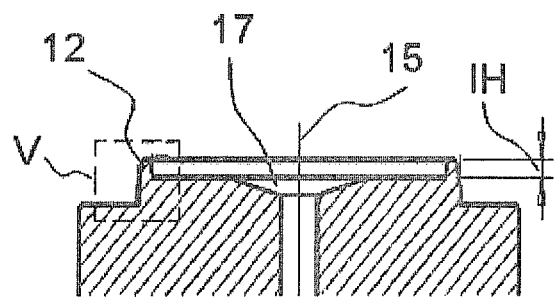
FIG. 4 is a side view in cross-section of a part of the clamping jaw shown in FIG. 3 on an enlarged scale.
Figure 5:
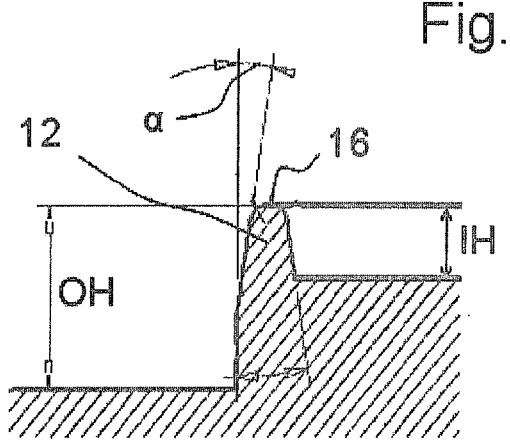
FIG. 5 is a side view in cross-section showing a portion of the part shown in FIG. 4 on a further enlarged scale.

In FIGS. 3-5 an example of one of the clamping jaws (clamping jaw 5) of the cartridge clamp of an assembly according to the invention is shown. The other clamping jaw 4 is constructed identically. These clamping jaws 4, 5, when clamping a cartridge body fully made of PEEK, provide an improved resistance against leakage at high liquid pressures. Such high liquid pressures are provided by means (forming part of the inventive assembly) for circulating a liquid through the closed circuit with a liquid pressure of at least 100 MPa. To ensure a proper sealing at such ultra high pressures the cartridge clamp is adapted for clamping said cartridge in-between the first and the second clamping face with a clamping force of at least 1500 N, preferably at least 1900 N, more preferably at least 2300 N, and most preferably of about 2500 N.

As shown, the clamping jaw 5 has a ring-shaped protrusion 12 extending around an axis 15 of one of the conduits. The protrusion 12 is arranged for contacting and deforming the respective end face of the cartridge 11 when the cartridge 11 is clamped between the clamping jaws 4, 5.

The ring-shaped protrusion 12 has a contact end face 16 for contacting a contact surface of the end face of the cartridge body 11. According to the invention the contact end face 16 of the ring-shaped protrusion 12 has a shape for creating a positive mechanical engagement between the clamping face, in particular the ring-shaped protrusion 12 thereof, and the respective contact surface of the respective end face of the cartridge body 11 during clamping of the cartridge between the clamping jaws.

In the presently most preferred embodiment the contact end face 16 of the ring-shaped protrusion 12 comprises a flat surface part, said flat surface part being parallel to the end face of the cartridge body during clamping. The radial dimension, in a direction perpendicular to the axis 15, of the flat surface part is, in the embodiment shown, 0.2 mm. However, in alternative embodiments the radial dimension can be between about 0.15 and about 0.25 mm and still provides proper sealing during clamping.

As clearly can be seen in FIG. 5 the edges of the flat surface part 16 are rounded. This facilitates loosening the cartridge from the clamping surface after SPE has been completed.

As indicated in FIG. 5 the ring-shaped protrusion 12 has an inner height IH and a larger outer height OH. In the most preferred embodiment the inner height is about 0.2 mm and the outer height is about 0.5 mm. As a result during clamping of the cartridge the PEEK material thereof is forced in a more radial outward direction, where the cartridge body 11 contains more material, which provides sufficient counter-pressure to ensure a correct positive mechanical engagement. In alternative embodiments the inner height can be between about 0.16 and 0.23 mm, and in further alternative embodiments the inner height can be equal to the outer height still providing proper sealing during SPE. Furthermore, it can be seen in FIG. 4 that the end face of the clamping jaw 5 radially inside the ring-shaped protrusion contains a circular depression 17 disposed coaxially around the axis 15. In particular when the cartridge 11 comprises a sealing membrane or sieve this circular depression ensures that during performing SPE the pressure applied by the liquid does not cause the membrane or sieve to be loosened from the cartridge.

As shown in FIG. 5 the ring-shaped protrusion 12 is slanted with an angle α of 10° facilitating loosening the cartridge from the clamping surface after SPE has been completed. In alternative embodiments (not shown) the angle can be between about 6 and 12°.

Due to the inventive ring-shaped protrusions the contact surfaces of the respective end faces of the cartridge 11 are at least partly deformed elastically when the cartridge 11 is clamped between the clamping jaws 4, 5. Thus, in a ring-shaped zone around the passage 13, a locally increased clamping force is generated and the PEEK material of the cartridge is effectively forced away to accommodate to the shape of the ring-shaped protrusions while providing sufficient counter-pressure against the ring-shaped protrusion to realize an effective sealing, due to a positive mechanical engagement which is obtained. Thus a particularly effective sealing is provided.

In the embodiment shown in the drawings the PEEK cartridge has a diameter of about 8 mm, and the passage 13 of the cartridge 11 has a diameter of about 1 mm (See FIG. 6). An optimal high pressure liquid tight sealing is then obtained, when the inner diameter of the ring-shaped protrusion is about 4 mm.

As is shown in the perspective view of FIG. 7 the cartridge 11 comprises a sieve 14 (or other sealing membrane) having a diameter of at most about 3 mm welded to an end face of the cartridge 11. The sieve 14 is substantially coaxial with the passage. As mentioned above the passage 13 bounded by the sieves can retain a sorbent. It is, however, in other embodiments also possible to provide a cartridge without sorbent in the passage 13 and or with no sieves or with one or both sieves mountable to the cartridge, for instance after a sorbent has been introduced into the passage.

The skilled person will appreciate that within the framework of the present invention as defined by the claims, many other variants than the examples and alternatives described above are conceivable. For instance, use can be made of a cartridge not containing any sorbent. Instead, the cartridge may for instance be packed with a filter material or be equipped with one or two or more closure membranes or sieves, the cartridge then constituting a filter or screen. Such a cartridge without sorbent can for instance be positioned in series with a cartridge containing sorbent.

In addition a person skilled in the art will, based on the description given above, realize that the cartridge body made of PEEK can be replaced by a cartridge completely made of a single material having a density, a Young's-modulus, a tensile strength, a water absorption, a thermal degradation and a chemical resistance substantially similar to PEEK.

The invention claimed is:

1. Assembly of a cartridge and a cartridge clamp, said cartridge having a cartridge body bounding a passage for retaining a sorbent, said passage extending from a first end face of the cartridge body to a second end face of the cartridge body, opposite the first end face of the cartridge body, said cartridge clamp having a first clamping jaw comprising a first clamping face and a second clamping jaw comprising a second clamping face, said first and second clamping faces being opposite of each other and facing each other, at least one clamping jaw being mounted to a slide movable along guides towards and away from the other clamping jaw, respectively, a first conduit being connected to the first clamping jaw and a second conduit being connected to the second clamping jaw, said conduits extending through the respective clamping jaw and each having an end aperture in the clamping face of the respective clamping jaw, said cartridge clamp being adapted for clamping said cartridge in-between the first and the second clamping face and for forming a closed circuit composed of the first conduit, the passage and the second conduit during clamping, each clamping face having a ring-shaped protrusion extending around the end aperture of the respective conduit, said protrusions being arranged for each contacting and deforming the end faces of the cartridge body when the cartridge is clamped between the clamping jaws with the passage of the cartridge aligned with the apertures in the clamping faces, wherein the cartridge body is completely made of PEEK or of a single material having a density, a Young's-modulus, a tensile strength, a water absorption, a thermal degradation and a chemical resistance substantially similar to PEEK, and in that each ring-shaped protrusion has a contact end face for contacting a contact surface of the end face of the cartridge body, said contact end face comprising a flat surface part, said flat surface part being parallel to the end face of the cartridge body during clamping for creating a positive mechanical engagement between the clamping face and the respective contact surface of said respective end face of the cartridge body during clamping of the cartridge between the clamping jaws.

2. An assembly according to claim 1, wherein the flat surface part has a radial dimension between about 0.15 and about 0.25 mm.

3. An assembly according to claim 2, wherein each of the edges of the flat surface part is rounded.

4. An assembly according to claim 1, wherein the assembly comprises means for circulating a liquid through the closed circuit with a liquid pressure of up to about 100 MPa, and wherein the cartridge clamp is adapted for clamping said cartridge in-between the first and the second clamping face with a clamping force of at least 1500 N.

5. An assembly according to claim 1, wherein each ring-shaped protrusion has a height between about 0.16 and 0.23 mm.

6. An assembly according to claim 1, wherein each ring-shaped protrusion is slanted with an angle between about 6° and 12°.

7. An assembly according to claim 1, wherein the cartridge has a diameter of about 8 mm, wherein the passage of the cartridge has a diameter of about 1 mm, and wherein the inner diameter of each ring-shaped protrusion is about 4 mm.

8. An assembly according to claim 1, wherein each ring-shaped protrusion has an inner height and an outer height, and wherein the inner height is smaller than the outer height.

9. An assembly according to claim 8, wherein the inner height is about 0.2 mm and the outer height is about 0.5 mm.

10. An assembly according to claim 1, wherein the cartridge comprises at least one sieve having a diameter of at most about 3 mm welded to an end face of the cartridge, said sieve being substantially coaxial with the passage.

11. A cartridge clamp for use in an assembly according to claim 1, wherein said cartridge clamp has a first clamping jaw comprising a first clamping face and a second clamping jaw comprising a second clamping face, said first and second clamping faces being opposite of each other and facing each other, at least one clamping jaw being mounted to a slide movable along guides towards and away from the other clamping jaw, respectively, a first conduit being connected to the first clamping jaw and a second conduit being connected to the second clamping jaw, said conduits extending through the respective clamping jaw and each having an end aperture in the clamping face of the respective clamping jaw, said cartridge clamp being adapted for clamping a cartridge having a cartridge body and a passage in-between the first and the second clamping face and for forming a closed circuit composed of the first conduit, the passage and the second conduit during clamping, each clamping face having a ring-shaped protrusion extending around the end aperture of the respective conduit, said protrusions being arranged for each contacting and deforming end faces of a cartridge body when a cartridge is clamped between the clamping jaws, wherein each ring-shaped protrusion has a contact end face comprising a flat surface part.

12. A cartridge clamp according to claim 11, wherein the flat surface part has a radial dimension between about 0.15 and about 0.25 mm.

13. A cartridge clamp according to claim 12, wherein each of the edges of the flat surface part is rounded.

14. A cartridge clamp according to claim 11, wherein the cartridge clamp is adapted for clamping a cartridge in-between the first and the second clamping face with a clamping force of at least 1500 N.

15. A cartridge clamp according to claim 11, wherein each ring-shaped protrusion has a height between about 0.16 and 0.23 mm.

16. A cartridge clamp according to claim 11, wherein each ring-shaped protrusion is slanted with an angle between about 6° and 12°.

17. A cartridge clamp according claim 11, wherein the cartridge has a diameter of about 8 mm, wherein the passage of the cartridge has a diameter of about 1 mm, and wherein the inner diameter of each ring-shaped protrusion is about 4 mm.

18. A cartridge clamp according to claim 11, wherein each ring-shaped protrusion has an inner height and an outer height, and wherein the inner height is smaller than the outer height.

19. A cartridge clamp according to claim 18, wherein the inner height is about 0.2 mm and the outer height is about 0.5 mm.

* * * * *